(12) United States Patent
Rao et al.

(10) Patent No.: US 7,732,597 B2
(45) Date of Patent: Jun. 8, 2010

(54) CRYSTALLINE FORM OF LINEZOLID

(75) Inventors: Dodda Mohan Rao, Hyderabad (IN); Pingili Krishna Reddy, Hyderabad (IN)

(73) Assignee: Symed Labs Limited, Hyderabad (IN)

( * ) Notice: Subject to any disclaimer, the term of this patent is extended or adjusted under 35 U.S.C. 154(b) by 129 days.

(21) Appl. No.: 11/861,406

(22) Filed: Sep. 26, 2007

(65) Prior Publication Data

US 2008/0090820 A1    Apr. 17, 2008

Related U.S. Application Data

(62) Division of application No. 10/524,478, filed as application No. PCT/IN03/00336 on Oct. 16, 2003.

(51) Int. Cl.
*C07D 413/00*    (2006.01)
(52) U.S. Cl. ....................................... 544/137
(58) Field of Classification Search ........................ None
See application file for complete search history.

(56) References Cited

U.S. PATENT DOCUMENTS

| 5,006,528 | A | 4/1991 | Oshiro |
| 5,688,792 | A | 11/1997 | Barbachyn et al. |
| 5,837,870 | A | 11/1998 | Pearlman et al. |
| 6,444,813 | B2 | 9/2002 | Bergren |
| 6,559,305 | B1 | 5/2003 | Bergren |
| 2006/0142283 | A1 | 6/2006 | Aronhime |

FOREIGN PATENT DOCUMENTS

| EP | 0367141 A2 | 10/1989 |
| WO | 99/24393 A1 | 5/1999 |
| WO | 01/70170 A1 | 9/2001 |
| WO | 02/085849 A2 | 10/2002 |
| WO | 2005/035530 A1 | 4/2005 |

OTHER PUBLICATIONS

Guillory, "Generation of Polymorphs, Hydrates, Solvates, and Amorphous Solids" in Polymorphism in Pharmaceutical Solids, vol. 95, Marcel Dekker, Inc., p. 183-226.*
Yasuo Oshiro, Novel Antipsychotic Agents wit Dopamine Autoreceptor Agonist Properties: Synthesis and Pharmacology of 7-[-4(4-Phenyl-1-piperazinyl)butoxyl03,4-dihydro-2(1H)-Quinolinone Derivatives, J. Med. Chem. 1998, 41, 658-667 PCT International Search Report dated Mar. 21, 2003.
European and Japanese Pharmacopoeias as part of the International Harmonization procedure (Pharmeuropa, vol. 14, No. 1, Jan. 2002, p. 185-191).
"Polymorphism in Pharmaceutical Solids", ed. H.G. Brittain, Marcel Dekker Inc. pp. 234-239.
Chawla et al. Challenges in Polymorphism of Pharmaceuticals, CRIPS vol. 5, No. 1, Jan.-Mar. 2004.
Braj B. Lohray, et al., A Short Synthesis of Oxazolidinone Derivative Linezolid and Eperezolid: A New Class of Antibacterials, Tetrahedron Leff, 40(26), 4855, 1999.
Steven J. Brickner, et al., Synthesis and Antibacterial Activity of U-100592 and U-100765, Two Oxazolidinone Antibacterial Agents for the Potential Treatment of Multidrgu Resistant Gram-Positive Bacterial Infections, J. Med. Chem, 39(3),673-679 (1996).
International Search Report dated Oct. 16, 2003.

* cited by examiner

*Primary Examiner*—Golam M. M. Shameem
*Assistant Examiner*—Sun Jae Y Loewe
(74) *Attorney, Agent, or Firm*—Caesar, Rivise, Bernstein, Cohen & Pokotilow, Ltd.

(57) ABSTRACT

The present invention relates to a novel crystalline form of linezolid, to processes for its preparation and to a pharmaceutical composition containing it.

22 Claims, No Drawings

CRYSTALLINE FORM OF LINEZOLID

This application is a Divisional of U.S. application Ser. No. 10/574,478, filed Feb. 22, 2005, which is a National Stage Entry of PCT/INO3/00336, filed Oct. 16, 2003.

FIELD OF THE INVENTION

The present invention relates to a novel crystalline form of linezolid, to processes for its preparation and to a pharmaceutical composition containing it.

BACKGROUND OF THE INVENTION

Linezolid, chemically N-[[(5S)-3-[3-fluoro-4-(4-morpholinyl)phenyl]-2-oxo-5-oxazolidinyl]methyl]acetamide is an antibacterial agent. Linezolid is represented by the following structure:

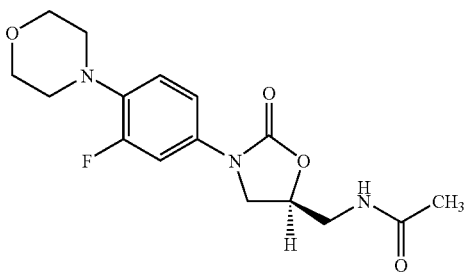

Linezolid and related compounds, processes for their preparation and their therapeutic uses were disclosed in U.S. Pat. No. 5,688,792. Processes for preparation of linezolid were also described in U.S. Pat. No. 5,837,870, WO 99/24393, J. Med. Chem. 39(3), 673-679, 1996 and Tetrahedron Lett., 40(26), 4855, 1999.

Linezolid is known to exhibit polymorphism and two crystalline forms are so far known. U.S. Pat. No. 6,559,305 and U.S. Pat. No. 6,444,813 addressed that the product obtained by the process described by J. Med. Chem. 39(3), 673-679, 1996 is form I and is characterized by having melting point of 181.5-182.5° C. and by IR spectrum having bands at 3284, 3092, 1753, 1728, 1649, 1565, 1519, 1447, 1435 cm$^{-1}$. U.S. Pat. No. 6,559,305 claims crystalline form II characterized by IR spectrum having bands at 3364, 1748, 1675, 1537, 1517, 1445, 1410, 1401, 1358, 1329, 1287, 1274, 1253, 1237, 1221, 1145, 1130, 1123, 1116, 1078, 1066, 1049, 907, 852 and 758 cm$^{-1}$ and powder X-ray diffraction spectrum having 2-theta values at 7.10, 9.54, 13.88, 14.23, 16.18, 16.79, 17.69, 19.41, 19.69, 19.93, 21.61, 22.39, 22.84, 23.52, 24.16, 25.28, 26.66, 27.01 and 27.77 degrees.

We have discovered a novel crystalline form (form III) of linezolid. The novel crystalline form of linezolid is consistently reproducible, does not have the tendency to convert to other forms and found to be thermally more stable than form I or form II. Furthermore, form III bulk solid is more compact and less electrostatic than form II and hence is more readily subjected to any treatment under the usual conditions of the pharmaceutical technology, in particular, of formulation on an industrial scale. Therapeutic uses of linezolid were disclosed in U.S. Pat. No. 5,688,792.

The object of the present invention is to provide a stable, consistently reproducible crystalline form of linezolid; processes for preparing it; and a pharmaceutical composition containing it.

SUMMARY OF THE INVENTION

In accordance with the present invention, there is provided a novel crystalline form of linezolid, designated as linezolid form III.

Linezolid form III is characterized by peaks in the powder x-ray diffraction spectrum having 2θ angle positions at about 7.6, 9.6, 13.6, 14.9, 18.2, 18.9, 21.2, 22.3, 25.6, 26.9, 27.9 and 29.9 degrees.

Linezolid form III is further characterized by IR spectrum having main bands at about 3338, 1741, 1662, 1544, 1517, 1471, 1452, 1425, 1400, 1381, 1334, 1273, 1255, 1228, 1213, 1197, 1176, 1116, 1082, 1051, 937, 923, 904, 869, 825 and 756 cm$^{-1}$.

Linezolid form III is obtained by heating linezolid in a known crystalline form or in a mixture of known crystalline forms until the known form/s are converted to form III.

The known form may be heated directly to obtain linezolid form III; or linezolid form III may be obtained by heating linezolid suspended in a solvent like toluene, xylene, etc.

The conversion to form III occurs at above about 90° C., preferably between 100° C. and 200° C. and more preferably between 120° C. and 140° C.

The heating takes at least about 30 min, usually about 2 hours to 12 hours and typically about 4 hours to 10 hours.

In accordance with the present invention, an alternative process is provided for preparation of linezolid form III, which comprises the steps of:
a) acetylating (S)—N-[[3-[3-fluoro-4-[4-morpholinyl] phenyl]-2-oxo-5-oxazolidinyl]methyl]amine of formula

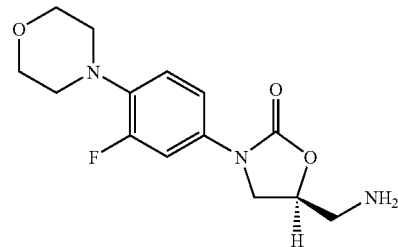

in a solvent optionally in the presence of an organic base to form linezolid;
b) optionally seeding the reaction mixture formed in step (a); and
c) isolating linezolid form III from the reaction mixture of (a) or (b);

wherein the solvent is selected from the group consisting of ethylacetate, methylacetate, propylacetate, isopropylacetate, butylacetate, acetonitrile, chloroform, methylenedichloride, benzene, toluene and xylene.

The organic base is preferably selected from pyridine; tri (C1-C4)alkylamine e.g. triethylamine and N.N-diisopropyl ethylamine; and N,N-di(C1-C3)alkylaniline e.g. N,N-dimethylaniline.

In accordance with the present invention, still another process is provided for preparation of linezolid form III, which comprises the steps of:
a) mixing linezolid with a solvent or a mixture of solvents;
b) cooling the contents to below about 15° C.;
c) optionally seeding the contents with linezolid form III;
d) stirring the contents for at least about 15 min; and e) collecting linezolid form III crystals by filtration or centrifugation;

wherein the solvent is selected from the group consisting of toluene, xylene, chloroform methylene dichloride, acetonitrile, water, $R_1$—OH, $R_1$—CO—$R_2$, $R_1$—CO—O—$R_2$, $R_1$—O—$R_2$ wherein $R_1$ and $R_2$ are independently $C_1$-$C_6$ alkyl groups. Preferable solvents are toluene, xylene, chloroform, methylene dichloride, acetonitrile, water, methanol, ethanol, propanol, isopropyl alcohol, tert-butyl alcohol, acetone, methyl ethyl ketone, ethylacetate, diethyl ether and methyl tert-butyl ether. Most preferable solvents are isopropyl alcohol and ethylacetate.

In accordance with the present invention, there is provided a pharmaceutical composition comprising linezolid form III and a pharmaceutically acceptable carrier or diluent.

DETAILED DESCRIPTION OF THE INVENTION

In accordance with the present invention, there is provided a novel crystalline form of linezolid, designated as linezolid form III.

Linezolid form III is characterized by peaks in the powder x-ray diffraction spectrum having 2θ angle positions at about 7.6, 9.6, 13.6, 14.9, 18.2, 18.9, 21.2, 22.3, 25.6, 26.9, 27.9 and 29.9 degrees.

Linezolid form III is further characterized by IR spectrum having main bands at about 3338, 1741, 1662, 1544, 1517, 1471, 1452, 1425, 1400, 1381, 1334, 1273, 1255, 1228, 1213, 1197, 1176, 1116, 1082, 1051, 937, 923, 904, 869, 825 and 756 cm$^{-1}$.

Linezolid form III is obtained by heating linezolid in a known crystalline form or in a mixture of known crystalline forms until the known form/s are converted to form III.

The known form may be heated directly to obtain linezolid form III; or linezolid form III may be obtained by heating linezolid suspended in a solvent like toluene, xylene, etc.

The conversion to form III occurs at above about 90° C., preferably between 100° C. and 200° C. and more preferably between 120° C. and 140° C.

The heating takes at least about 30 min, usually about 2 hours to 12 hours and typically about 4 hours to 10 hours.

No recimization occurs during the heating of linezolid as evidenced by enantiomeric purity, which is same before and after heating.

In accordance with the present invention, an alternative process is provided for preparation of linezolid form III.

Thus, (S)—N-[[3-[3-fluoro-4-[4-morpholinyl]phenyl]-2-oxo-5-oxazolidinyl]methyl]amine of formula

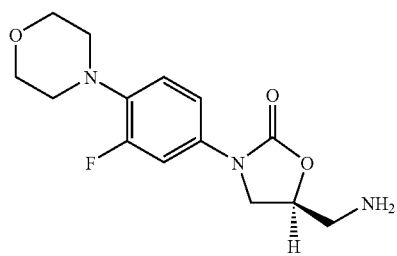

is reacted with an acetylating agent, like acetic anhydride, acetyl chloride, in a solvent optionally in the presence of an organic base and linezolid formed is isolated from the reaction mixture.

The solvent is selected from the group consisting of ethylacetate, methylacetate, propylacetate, isopropylacetate, butylacetate, acetonitrile, chloroform, methylenedichloride, benzene, toluene and xylene.

The organic base is preferably selected from pyridine; tri (C1-C4)alkylamine e.g. triethylamine and N,N-diisopropyl ethylamine; and N.N-di(C1-C3)alkylaniline e.g. N,N-dimethylaniline.

Preferably, (S)—N-[[3-[3-fluoro-4-[4-morpholinyl]phenyl]-2-oxo-5-oxazolidinyl]methyl]amine is mixed in ethyl acetate, acetic anhydride is added maintaining the reaction temperature at or below boiling temperature of ethylacetate, preferably at about 15° C. to 40° C.; the reaction mixture is agitated preferably at about 15° C. to 40° C. for at least 15 min; and linezolid form III is collected by filtration or centrifugation.

The reaction mixture is optionally seeded with linezolid form III before isolating linezolid form III.

In accordance with the present invention, still another process is provided for preparation of linezolid form III.

Thus, linezolid is mixed with a solvent. Linezolid is preferably mixed at boiling point of the solvent used. The solvent is selected from the group consisting of toluene, xylene, chloroform methylene dichloride, acetonitrile, water, $R_1$—OH, $R_1$—CO—$R_2$, $R_1$—CO—O—$R_2$, $R_1$—O—$R_2$ wherein $R_1$ and $R_2$ are independently $C_1$-$C_6$ alkyl groups. Preferable solvents being toluene, xylene, chloroform, methylene dichloride, acetonitrile, water, methanol, ethanol, propanol, isopropyl alcohol, tert-butyl alcohol, acetone, methyl ethyl ketone, ethylacetate, diethyl ether and methyl tert-butyl ether. Most preferable solvents being isopropyl alcohol and ethylacetate. A mixture of solvents may also be used and solvents like hexane, heptane may also be added in order to enhance crystallization in latter stages. Linezolid obtained by a known method is used in the process.

The solution obtained as above is cooled to below about 15° C., preferably to about 0° C. to about 15° C., more preferably to about 0° C. to about 10° C.

The contents are optionally seeded with linezolid form III.

The contents are then stirred for at least about 15 min, preferably for about 30 min to 8 hours and more preferably about 1 hour to about 5 hours.

Linezolid form III crystals are then collected by filtration or centrifugation.

In accordance with the present invention, there is provided a pharmaceutical composition comprising linezolid form III and a pharmaceutically acceptable carrier or diluent.

The invention will now be further described by the following examples; which are illustrative rather than limiting.

EXAMPLE 1

Linezolid (10 gm, obtained by the process described in U.S. Pat. No. 5,688,792 Example 5) is heated at 130° C. to 140° C. under $N_2$ atmosphere for 4 hours to give linezolid form III quantitatively.

EXAMPLE 2

Linezolid form II (10 gm, with 99.8% ee) is suspended in toluene (50 ml) and refluxed for 3 hours. the contents are cooled to 25° C. and filtered to obtain 9.8 gm of linezolid form III (99.8% ee).

EXAMPLE 3

Linezolid (10 gm, obtained by the process described in U.S. Pat. No. 5,688,792 Example 5) is mixed with isopropyl alcohol (200 ml), heated to 80° C. and stirred for 10 min at the same temperature to form a clear solution. The solution is cooled to 0° C., stirred for 1 hour 30 min at 0° C. and filtered to give 9.7 gm of linezolid form III

EXAMPLE 4

Example 3 is repeated by seeding the solution with linezolid form III during maintenance at about 0° C. Yield of linezolid form III is 9.6 gm.

EXAMPLE 5

To the mixture of (S)—N-[[3-[3-fluoro-4-[4-morpholinyl]phenyl]-2-oxo-5-oxazolidinyl]methyl]amine (10 gm) and ethylacetate (100 ml), acetic anhydride (10 ml) is slowly added at ambient temperature, then stirred at ambient temperature for 1 hour. The separated solid is filtered and dried under reduced pressure at 50° C. to give 9.5 gm of linezolid form III.

We claim:

1. A process for preparation of linezolid form III, characterized by peaks in the powder x-ray diffraction spectrum having 2θ angle positions at about 7.6, 9.6, 13.6, 14.9, 18.2, 18.9, 21.2, 22.3, 25.6, 26.9, 27.9 and 29.9 degrees, which comprises the steps of:
   (a) acetylating (S)—N-[[3[3-fluoro-4[4-morpholinyl]phenyl]-2-oxo-5-oxazolidinyl]methyl]amine of formula

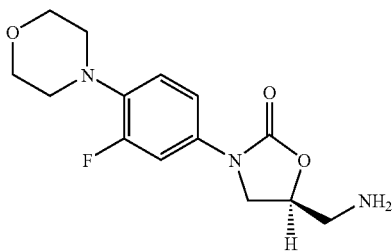

in a solvent optionally in the presence of an organic base to form linezolid;
   b) optionally seeding the reaction mixture formed in step (a); and
   c) isolating linezolid form III from the reaction mixture of (a) or (b);

wherein the solvent is selected from the group consisting of ethylacetate, methylacetate, propylacetate, isopropylacetate, butylacetate, toluene and xylene.

2. A process according to claim 1, wherein the process is cared out in the presence of the organic base.

3. A process according to claim 1, wherein the organic base is selected from pyridine, tri(C1-C4)alkylamine and N,N-di(C1-C3)alkylaniline.

4. A process according to claim 3, wherein the organic base is pyridine, triethylamine, N,N-diisopropyl ethylamine and N,N-dimethylaniline.

5. A process according to claim 1, wherein the process is cared out in the absence of the organic base.

6. A process according to any one of claims 1-5, wherein the solvent is ethylacetate.

7. A process according to any one of claims 1-5, wherein linezolid form III is isolated without seeding.

8. A process according to claim 1-5, wherein linezolid form III is isolated after seeding.

9. A process according to claim 2, wherein the solvent is ethylacetate.

10. A process according to claim 3, wherein the solvent is ethylacetate.

11. A process according to claim 4, wherein the solvent is ethylacetate.

12. A process according to claim 5, wherein the solvent is ethylacetate.

13. A process according to claim 2, wherein linezolid form III is isolated without seeding.

14. A process according to claim 3, wherein linezolid form III is isolated without seeding.

15. A process according to claim 4, wherein linezolid form III is isolated without seeding.

16. A process according to claim 5, wherein linezolid form III is isolated without seeding.

17. A process according to claim 1, wherein linezolid form III is isolated without seeding.

18. A process according to claim 2, wherein linezolid form III is isolated after seeding.

19. A process according to claim 3, wherein linezolid form III is isolated after seeding.

20. A process according to claim 4, wherein linezolid form III is isolated after seeding.

21. A process according to claim 5, wherein linezolid form III is isolated after seeding.

22. A process according to claim 1, wherein linezolid form III is isolated after seeding.

* * * * *